United States Patent [19]
Kim et al.

[11] Patent Number: 6,071,525
[45] Date of Patent: Jun. 6, 2000

[54] WHITENING COSMETICS CONTAINING MULBERRIN

[76] Inventors: Jeong-Ha Kim, 1-804, Samho Apt., Bangbae-dong, Seocho-gu, Seoul; Kang-Tae Lee, 102-704, Hando Apt., Jiksan-kun, Cheonan-si, Chungcheongnam-do, both of Rep. of Korea

[21] Appl. No.: 09/138,693

[22] Filed: Aug. 24, 1998

[30] Foreign Application Priority Data

Dec. 9, 1997 [KR] Rep. of Korea .................. 97-47260

[51] Int. Cl.$^7$ .............................. A61K 7/00; A61K 31/35
[52] U.S. Cl. .................. 424/401; 424/62; 424/195.1; 514/460; 514/844
[58] Field of Search .................. 424/401, 62, 195.1; 514/460, 844

[56] References Cited

PUBLICATIONS

Nomura et al., "On The Structures of Mulberrin, Mulberrochromene, Cyclomulberrine, and Cyclomulberrochromene", *Heterocycles*, vol. 12 (1979).

Chari et al, "$^{13}$C NMR Spectra of Chromeno–and Prenylated Flavones Structure Revisions of Mulberrin, Mulberrochromene, Cyclomulberrin and Cyclomulberrochromeme", *Z. Naturforsch.* 33b, 1547–1549 (1978).

*Primary Examiner*—Michael A. Williamson
*Attorney, Agent, or Firm*—Duane, Morris & Heckscher LLP

[57] ABSTRACT

The present invention relates to cosmetic products having a whitening effect, which comprises mulberrin.

According to the present invention, an aqueous suspension of the *Ramulus mori* extract, which have been obtained by extracting young branches of plants belonged to Morus genus with water or an organic solvent, is fractionated by organic solvents, isolated and purified to give mulberrin, which is then added to conventional skin-care cosmetics to give whitening cosmetics having an excellent whitening effect.

5 Claims, No Drawings

WHITENING COSMETICS CONTAINING MULBERRIN

FIELD OF THE INVENTION

The present invention relates to cosmetic products having a whitening effect, which contains mulberrin represented below by Formula 1:

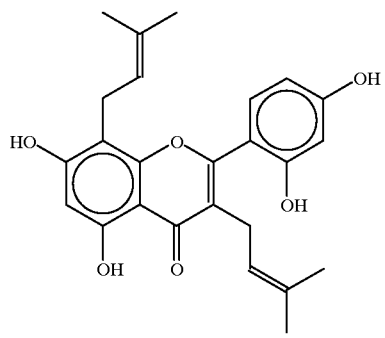

BACKGROUND OF THE INVENTION

Every living organism exhibits various responses against the external environment in order to maintain the homeostasis of life. The synthesis of melanin also relates to this phenomenon.

In general, there are various reasons for the darkening of skin color, the main reason being ultraviolet rays. When skin is exposed to ultraviolet rays, melanin is synthesized in melanocytes, which is a type of skin cell, and released to darken skin color. In the process of melanin synthesis in melanocytes, tyrosinase reacts on tyrosine, which is a substrate for tyrosinase, in the cell to yield Dopaquinone and it goes through sequential oxidation to give Dopachrome and then 5,6-dihydrozyindole (DHI) and 5,6-dihydroxyindol-2-carboxylic acid (DHICA), the monomers of melanin, which are then polymerized with each other to provide a copolymeric black pigment, melanin. Thus, an understanding of the mechanism of melanin synthesis is very important to the development of whitening agents or cosmetic products having whitening effect. In other words, the interpretation of the melanin-control mechanism may provide a method of preventing color deposition by melanin. In order to prevent darkening of skin color (for example, liver spots, freckles, or the like), it is most simple and general to inhibit a step of the process of generating melanin, and to reduce the production of melanin. Such inhibition can be performed by inhibiting the activity of tyrosinase.

At present, research activity to develop an agent with tyrosinase-inhibiting activity is intensive. Representatives of inhibiting agents include kojic acid, arbutin, hydroquinone, Vitamin C, *Cortex mori*, and licorice root extract.

Among these, kojic acid forms a chelate with a copper ion at the active site of tyrosinase to inhibit the enzyme activity. Though it has high activity, it is not appropriate for use in cosmetics because of stability problems in the process of blending in cosmetic products.

Ascorbic acid (vitamin C) and its derivatives have relatively low activity in inhibition of tyrosinase.

Hydroquinone is not desirable in that it has irreversible whitening activity and irritates the skin strongly, so that its use as a cosmetic material has been restricted in the past. Furthermore, hydroquinone has recently been recognized as a carcinogen, so that its use in cosmetic products is now prohibited.

Many plant extracts have demonstrated substantial inhibition effect on tyrosinase activity, when used in high concentrations. When used in relatively low concentrations, tyrosinase inhibition activity is hardly seen to occur.

In view of the above, the present inventors have performed intensive studies for finding a superior and excellent whitening agent which avoids the problems of conventional whitening agents. As a result of searching for an effective material having whitening activity among the natural plants of which the safety has been already proved as they have been used in herb remedies or folk remedies for a long time, it has been found that the extracts of *Ramulus mori*, young twigs of plants belonging to Morus genus, show excellent inhibiting activity on tyrosinase. The results of these studies have been filed as an invention with the Korea Industrial Property Office [Korean Patent Application No. 97-4913]. However, the actual compound having inhibition effect on tyrosinase activity among the materials contained in *Ramulus mori* has not been described in the above patent application. Thus, the development of an excellent and superior inhibiting agent for melanin synthesis by isolating and purifying the tyrosinase-inhibiting components of *Ramulus mori* is still urgently required.

SUMMARY OF THE INVENTION

In order to find an effective component having tyrosinase-inhibiting activity, from *Ramulus mori*, in accordance with the present invention, intensive studies have been continuously performed, resulting in the isolation of material exhibiting very strong inhibition effect of melanin synthesis. As a result of analysis of this material, it is found that it is mulberrin, a known compound.

Mulberrin has been previously isolated from *Cortex mori* and identified by Nomura et al. (*Heterocycles*, 14(12), 1943–1951 (1980); *Heterocycles*, 15(2), 1531–1567 (1981)). The compound prepared by the present invention was also identified as the same compound (mulberrin) by mass spectroscopy, IR, UV and NMR.

The object of the present invention is to provide whitening cosmetic products having an excellent and superior whitening effect while avoiding problems associated with conventional tyrosinase activity inhibitors, by incorporating mulberrin in conventional skin-care products.

DETAILED DESCRIPTION OF THE INVENTION

Mulberrin, which is contained in whitening cosmetic products in accordance with the present invention, can be prepared as follows:

*Ramulus mori* extracts, which have been obtained by conventionally extracting young twig of plants belonging to the Morus genus with water or a mixture of organic solvents, is concentrated to dryness by using a rotary evaporator under reduced pressure, with water then being added to the concentrate to form a suspension. The suspension is then sequentially extracted with organic solvents such as chloroform, ethyl acetate and butanol to provide fractions, which are separated by an analytic process such as chromatography to isolate the pure compound, mulberrin.

As described above, *Ramulus mori* used in the present invention is obtained from dried young twig of plants belonging to the Morus genus. Morus genus includes *Morus alba*, Linne; *Morus alba* for. Pelldullus DIPPEL; *Morus bombycis*, Koidzumi; *Morus bombycis* var. *Caudatifolia*; *Morus bombycis* var. *martitima* KOIDZ; *Morus bombycis* for. Kase VYKEI; *Morus tiliaefolia*, Makino; etc. Among these, *Ramulus mori* obtained from Korean mulberry trees is most preferable because of the high content of inhibiting material against tyrosinase activity. In the present invention, mulberrin obtained by a chemical synthetic process may be used as well, in like manner as mulberrin isolated and purified from *Ramulus mori*.

In accordance with the invention, mulberrin prepared as described above can be added to any of the numerous conventional cosmelics, especially skin care cosmetics, such as, without limitation, skin softener (skin lotion), astringent, nutrient emulsion (milk lotion), nutrient cream, massage cream, essence and facial pack. In accordance with this invention, the amount of mulberrin added may preferably range from about 0.00001% to about 5% (w/w), and more preferably from about 0.001% to about 1% (w/w), based on the dry weight of each cosmetic product.

These ranges are, of course, not critical and may range higher or lower, depending upon particular cosmetic application contemplated.

PREFERRED EMBODIMENTS OF THE INVENTION

The present invention is now described with reference to Examples and Experimental Examples. However, it should noted that these examples are intended to be illustrative in nature only, and are not intended to limit or restrict the scope of this invention or the claims in any way.

EXAMPLE 1

Isolation and Identification of Mulberrin

*Ramulus mori* (1 kg) was extracted with ethanol (5 L), and the extract concentrated to dryness by using a rotary evaporator under reduced pressure. Distilled water was then added to the concentrate to give an aqueous suspension. The suspension was then sequentially extracted with chloroform, ethyl acetate and butanol to give fractions. The ethyl acetate fraction was purified by Sephadex LH-20 chromatography and silica gel chromatography to obtain the desired compound, mulberrin.

The results from mass spectroscopy analysis, IR, UV and NMR analysis of the resulting compound are shown below:

recrystallization (solvent: ether/benzene): pale yellow prism; MS m/z: 422, 407, 379, 367, 323; UV $\lambda_{max}^{etOH}$: 210 nm, 264 nm, 315 nm; IR: 3370, 1660, 1630, 1610, 1560; $^1$H-NMR(CD$_3$COCD$_3$) δ; 1.43 (3H, s, C$_{11}$-CH$_3$), 1.57(9H, s, C$_{11}$-CH$_3$ and C$_{14}$-CH$_3$×2), 3.12(2H, br d, J=8 Hz, C$_9$-H×2), 3.35(2h, brd,J=8 Hz, C$_{12}$-H×2), 5.20(2H,m,C$_{10}$ and C$_{13}$-H), 6.31(1H, s, C$_6$-H), 6.43(1H, dd, J=2 and 8 Hz, C$_5$'-H),6.52 (1H, d, J=2 Hz, C$_3$'-H), 7.20(1H, d, J=8 Hz, C$_6$'-H), 13.05 (1H, s, OH); m.p.: 148~150° C.

As shown in Table 1 below, the numbers in parentheses are $^{13}$C-NMR values of mulberrin isolated from *Cortex mori* by the methods described in Nomura et al. It is found that the material obtained according to the present invention is mulberrin having molecular weight of 422.

TABLE 1

$^{13}$C-NMR of Mulberrin

| | Mulberrin<br>Unit: δ (ppm, DMSO, d$_6$) |
|---|---|
| C-2 | 159.1(158.9) |
| 3 | 119.6(119.4) |
| 4 | 182.1(181.8) |
| 4$_a$ | 103.4(103.4) |
| 5 | 155.1(155.0) |
| 6 | 98.2(97.9) |
| 7 | 161.9(161.7) |
| 8 | 105.6(105.5) |
| 8$_9$ | 160.2(160.3) |
| 9 | 23.4(23.5) |
| 10 | 121.9(121.7) |
| 11 | 131.6(131.2) |
| 12 | 25.6(25.4) |
| 13 | 17.4(17.3) |
| 14 | 21.2(21.1) |
| 15 | 122.3(122.1) |
| 16 | 130.9(131.7) |
| 17 | 25.6(25.4) |
| 18 | 17.4(17.3) |
| C-1' | 111.6(111.3) |
| 2' | 156.8(156.5) |
| 3' | 102.8(102.7) |
| 4' | 161.6(161.2) |
| 5' | 106.8(106.7) |
| 6' | 131.6(131.2) |

Experimental Example 1

Tyrosinase Inhibition Effect of Mulberrin

The inhibition effect of mulberrin obtained from Example 1 on tyrosinase activity was determined as follows:

In this Example, a tyrosinase, commercially available from Sigma Co. which has been separated from mushroom and purified, was used. The substrate, tyrosine was used as a solution (0.1 mg/ml) dissolved in 0.05 M sodium phosphate buffer (pH 6.8). The inhibiting compound of the present invention (mulberrin 0.5 ml) was mixed therein and the mixture was placed in an incubator at 37° C. for 10 minutes. Then 200 U/ml tyrosinase (0.5 ml) was added thereto, and the reaction performed at the same temperature for 10 minutes. As a control group, buffer solution (0.5 ml) was added instead of the compound. The reaction was quenched by placing the test tube containing the reaction mixture on ice. Absorbance was measured at a wavelength of 475 nm by using a spectrophotometer.

The inhibition effects of the test compound on tyrosinase activity was determined by the equation below:

Inhibition Ratio of Tyrosinase Activity (%)=100−(100×Absorbance When Mulberrin Added/Absorbance of Control Group)

The experimental results are shown in Table 2.

TABLE 2

Tyrosinase Inhibition Effects of Test Materials

| Test Material | IC$_{50}$: μg/ml<br>(concentration required for 50% inhibition of tyrosinase activity) |
|---|---|
| Mulberrin | 0.50 |
| *Ramulus mori* | 12.48 |

TABLE 2-continued

Tyrosinase Inhibition Effects of Test Materials

| Test Material | $IC_{50}$: μg/ml (concentration required for 50% inhibition of tyrosinase activity) |
|---|---|
| extracts | |
| Kojic acid | 5.82 |
| Arbutin | 65.20 |

Experimental Example 2

Effect of Mulberrin for Melanin Synthesis in Melanocytes

As melanocytes, commercially available B-16 melanoma (ATCC CRL 6323) cell line derived from mouse was used. The melanoma cell line was inoculated in DMEM culture medium containing glucose (4.5 g/l), 10% serum and 1% antibiotic agent, and cultivated in a 50 ml T-flask at 37° C. After cultivation under a condition of 5% $CO_2$ for 24 hours, the culture solution was treated with 0.05% trypsin containing 0.02% EDTA to isolate cells, which was then inoculated in a 50 ml T-flask and cultivated for 48 hours. At this time, the number of cells was $5.76 \times 10^6$ cells/flask. A diluted solution of mulberrin in DMEM medium at a proper concentration was incorporated to the cultivated melanoma cells, and the mixture was cultivated at 37° C. for 5 days. After finishing cultivation, culture medium was thoroughly removed, and the residue was treated with 1 ml of saline-phosphate buffer solution (PBS) containing 0.02% EDTA and 0.05% trypsin to isolate cells, which were then centrifuged for 5 minutes to collect pure cells. The obtained cells were treated with a solution of 5% trichloroacetate (TCA), stirred, and centrifuged. Precipitated melanin was washed with saline-phosphate buffer solution, and treated with 1N NaOH to dissolve melanin therein. Absorbance at 475 nm was measured. Melanin concentration was determined from standard concentration curve of synthetic melanin (produced by Sigma).

The experimental results are shown below in Table 3.

TABLE 3

Effect of Mulberrin for Melanin Synthesis in Melanocytes

| Concentration of mulberrin (μg/ml) | Content of melanin (pg/cell) | Inhibition ratio of melanin synthesis (%) |
|---|---|---|
| no add | 4.28 | — |
| 10 | 1.95 | 54.4 |
| 20 | 1.42 | 66.8 |
| 50 | 1.07 | 74.8 |
| 100 | 0.46 | 89.3 |

The results show that the mulberrin is a strong whitening agent inhibiting melanin synthesis in melanocytes.

Formulation 1

An exemplary formula of a skin softener containing mulberrin in accordance with the present invention is shown below.

| COMPONENT | CONTENT (%, w/w) |
|---|---|
| mulberrin | 0.1 |
| glycerin | 5.0 |
| 1,3-butylene glycol | 3.0 |
| PEG 1500 | 1.0 |
| alantoin | 0.1 |
| DL-panthenol | 0.3 |
| EDTA-2Na | 0.02 |
| benzophenone-9 | 0.04 |
| sodium hyaluronate | 5.0 |
| ethanol | 10.0 |
| octicdodeces-16 | 0.2 |
| polysorbate 20 | 0.2 |
| preservatives, fragrance, pigment | small quantity |
| distilled water | residual quantity |
| Total | 100 |

Formulation 2

An exemplary formula of a astringent produced in accordance th the invention is shown below.

| COMPONENT | CONTENT (%, w/w) |
|---|---|
| mulberrin | 0.1 |
| glycerin | 2.0 |
| 1,3-butylene glycol | 2.0 |
| alantoin | 0.2 |
| DL-panthenol | 0.2 |
| EDTA-2Na | 0.02 |
| benzophenone-9 | 0.04 |
| sodium hyaluronate | 3.0 |
| ethanol | 15.0 |
| polysorbate 20 | 0.3 |
| witch hazel extracts | 2.0 |
| citric acid | small quantity |
| preservatives, fragrance, pigment | small quantity |
| distilled water | residual quantity |
| Total | 100 |

Formulation 3

An exemplary formula of a nutrient emulsions shown below.

| COMPONENT | CONTENT (%, w/w) |
|---|---|
| mulberrin | 0.5 |
| glyceryl stearate SE | 1.5 |
| stearyl alcohol | 1.5 |
| lanolin | 1.5 |
| polysorbate 60 | 1.3 |
| sorbitan sesquioleate | 0.5 |
| hydrogenated vegetable oil | 1.0 |
| mineral oil | 5.0 |
| squalane | 3.0 |
| trioctanoin | 2.0 |
| dimethicone | 0.8 |
| tocopherol acetate | 0.5 |
| carboxyvinyl polymer | 0.12 |
| glycerin | 5.0 |
| 1,3-butylene glycerol | 3.0 |
| sodium hyaluronate | 5.0 |
| triethanol amine | 0.12 |
| preservatives, fragrance, pigment | small quantity |
| distilled water | residual quantity |
| Total | 100 |

Formulation 4

An exemplary formula of a nutrient cream prepared in accordance with this is shown below.

| COMPONENT | CONTENT (%, w/w) |
|---|---|
| mulberrin | 0.1 |
| glycerin monostearate | 2.0 |
| stearyl alcohol | 2.2 |
| stearic acid | 1.5 |
| wax | 1.0 |
| polysorbate 60 | 1.5 |
| sorbitan stearate | 0.6 |
| hydrogenated vegetable oil | 1.0 |
| squalane | 3.0 |
| mineral oil | 5.0 |
| trioctanoin | 5.0 |
| dimethicone | 1.0 |
| sodium magnesium silicate | 0.1 |
| glycerin | 5.0 |
| betaine | 3.0 |
| triethanol amine | 1.0 |
| sodium hyaluronate | 4.0 |
| preservatives, fragrance, pigment | small quantity |
| distilled water | residual quantity |
| Total | 100 |

Formulation 5

An exemplary formula of a massage cream prepared in accordance with this invention is shown below.

| COMPONENT | CONTENT (%, w/w) |
|---|---|
| mulberrin | 0.1 |
| glycerin monostearate | 1.5 |
| stearyl alcohol | 1.5 |
| stearic acid | 1.0 |
| polysorbate 60 | 1.5 |
| sorbitan stearate | 0.6 |
| isostearyl isostearate | 5.0 |
| squalane | 5.0 |
| mineral oil | 35.0 |
| dimethicone | 0.5 |
| hydroxyethyl cellulose | 0.12 |
| glycerin | 6.0 |
| triethanol amine | 0.7 |
| preservatives, fragrance, pigment | small quantity |
| distilled water | residual quantity |
| Total | 100 |

Formulation 6

An exemplary formula of an essence prepared in accordance with this invention is shown below.

| COMPONENT | CONTENT (%, w/w) |
|---|---|
| mulberrin | 0.5 |
| glycerin | 10.0 |
| betaine | 5.0 |
| PEG 1500 | 2.0 |
| alantoin | 0.1 |
| DL-panthenol | 0.3 |
| EDTA-2NA | 0.02 |
| benzophenon-9 | 0.04 |
| hydroxyethyl cellulose | 0.1 |
| sodium hyaluronate | 8.0 |
| carboxyvinyl polymer | 0.2 |
| triethanol amine | 0.18 |
| octyldodecanol | 0.3 |
| octyldodeces-16 | 0.4 |
| ethanol | 6.0 |
| preservatives, fragrance, pigment | small quantity |
| distilled water | residual quantity |
| Total | 100 |

Formulation 7

An exemplary formula of a facial pack is shown below.

| COMPONENT | CONTENT (%, w/w) |
|---|---|
| mulberrin | 0.5 |
| polyvinyl alcohol | 15.0 |
| cellulose gum | 0.15 |
| glycerin | 3.0 |
| PEG 1500 | 2.0 |
| cyclodextrin | 0.15 |
| DL-panthenol | 0.4 |
| alantoin | 0.1 |
| monoammonium glycyrrhizinate | 0.3 |
| nicotinamide | 0.5 |
| ethanol | 6.0 |
| PEG 40 hydrogenated castor oil | 0.3 |
| preservatives, fragrance, pigment | small quantity |
| distilled water | residual quantity |
| Total | 100 |

Mulberrin obtained according to the present invention exhibits a much more intensive whitening effect than conventional whitening agents such as *Cortex mori*, kojic acid, arbutin and the *Ramulus mori* extract which had previously been developed by the present inventors. This compound also exhibits a very excellent effect in inhibiting melanin synthesis.

What is claimed is:

1. A cosmetic product having a skin-whitening effect which comprises mulberrin in a tyrosinase-inhibiting effective amount.

2. A cosmetic product having a skin-whitening effect according to claim 1, wherein mulberrin is present in an amount of from about 0.00001% to about 5% (w/w) of the dry weight of the cosmetic product.

3. A cosmetic product having a skin-whitening effect according to claim 1, wherein mulberrin is present in an amount of from about 0.001% to about 1% (w/w) of the dry weight of the cosmetic product.

4. A cosmetic product having a skin-whitening effect according to claim 1, wherein said mulberrin is obtained by concentrating a *Ramulus mori* extract, which has been obtained by conventional extraction thereof with water or a mixed solvent of organic solvents to dryness;

suspending the concentrate in purified water;

sequentially extracting the suspension with chloroform, ethyl acetate and butanol to give fractions; and separating the fractions by analytical chromatography.

5. A cosmetic product having skin-whitening effect according to claim 1, wherein the product is in the form of skin softener, astringent, nutrient emulsion (milk lotion), nutrient cream, massage cream, essence, or facial pack.

* * * * *